United States Patent [19]
Charm et al.

[11] Patent Number: 5,489,532
[45] Date of Patent: Feb. 6, 1996

[54] AUTOMATIC TEST APPARATUS FOR ANTIMICROBIAL DRUGS

[75] Inventors: Stanley E. Charm, Boston; Eliezer Zomer, Quincy; Thomas Lieu, Malden; Max Gandman, Malden; Lee Gandman, Malden, all of Mass.

[73] Assignee: Charm Sciences, Inc., Malden, Mass.

[21] Appl. No.: 203,011

[22] Filed: Feb. 28, 1994

Related U.S. Application Data

[60] Division of Ser. No. 791,785, Nov. 12, 1991, Pat. No. 5,354,663, which is a continuation-in-part of Ser. No. 614,729, Nov. 16, 1990, abandoned, which is a continuation of Ser. No. 190,041, May 4, 1988, abandoned.

[51] Int. Cl.⁶ .............. C12Q 1/00; C12Q 1/02; C12Q 3/00; C12M 1/36
[52] U.S. Cl. .......... 435/286.1; 165/6; 165/48.1; 165/50; 165/53; 165/86; 220/507; 220/515; 220/516; 220/577; 422/68.1; 422/104; 422/119; 422/173; 422/300; 435/287.1; 435/809; 435/287.3; 435/288.4; D23/323
[58] Field of Search .................. 435/287, 289, 435/300, 809, 32, 29; 422/68.1, 99, 100, 102, 104, 119, 173, 198, 300; 220/377, 507, 515, 516; D23/323; 165/6, 48.1, 50, 53, 86, 920

[56] References Cited

U.S. PATENT DOCUMENTS

| | | | |
|---|---|---|---|
| 4,753,892 | 6/1988 | Loombs | 436/183 |
| 5,061,448 | 10/1991 | Mahe et al. | 422/104 |

OTHER PUBLICATIONS

Fisher Catalog (1992) pp. 988–989, 1224 Fisher Scientific, Pgh. Pa.

*Primary Examiner*—Michael G. Wityshyn
*Assistant Examiner*—Jane Williams
*Attorney, Agent, or Firm*—Richard P. Crowley

[57] ABSTRACT

An automatic test apparatus for use in a test method to determine antimicrobial drugs. The test apparatus comprises a first aluminum, electrically heatable block with holes for the insertion of test containers and a separate, second cooling aluminum block adapted to be placed periodically in contact with the heated aluminum block to cool rapidly the heated block. The test apparatus includes timed signals existing therein to alert the test user. The test apparatus is adapted to provide for the timed sequential solid heating and cooling of one or more test containers containing a test sample.

13 Claims, 14 Drawing Sheets

AUTOMATIC TEST APPARATUS FOR ANTIMICROBIAL DRUGS

REFERENCE TO PRIOR APPLICATIONS

This is a divisional of application Ser. No. 07/791,785 filed on Nov. 12, 1991, (U.S. Pat. No. 5,354,663) which is a continuation-in-part of Ser. No. 07/614,729, filed Nov. 16, 1990, which is now abandoned, which is a continuation of Ser. No. 07/190,041, filed May 4, 1988, now abandoned.

BACKGROUND OF THE INVENTION

Antimicrobial drugs, particularly those used in animal feed or to treat animals, have been found in milk and food products, such as for example, beta lactams like penicillin and/or tetracyclines, and more recently sulfa drugs like sulfonamides, such as sulfamethazine, have been detected in food products. The detection of these drugs at low levels are most important, particularly sulfa drugs which are allergenic and possibly carcinogenic in nature, even at low levels. Milk is routinely tested for the presence of drugs, like beta lactam, by the use of an inhibition disc assay method. However, such assay method does not detect sulfa drugs or certain other antimicrobial drugs at very low levels.

One technique for detecting sulfa drugs in milk at low levels is by the employment of high pressure liquid chromatography (HPLC) or by receptor assay test method (see U.S. Pat. Nos. 4,239,745 and 4,239,852, both issued Dec. 16, 1980). Both of such test methods are cumbersome and require costly equipment and highly trained technicians.

A microbiological growth inhibition test method to detect sulfonamides in milk for example has been reported and described in European patent specification 79200277.6 by Beukers et al, published Dec. 12, 1979. This test method has been described as an improvement on the test described in British patent specification 1 467 439, published Mar. 16, 1977 to Lameris et al. The Beukers et al test method places spores of *Bacillus stearothermophilus* (BST) into a buffered agar solution, and the agar is solidified to form a support medium. The BST in the agar solution is prevented from germinating by lack of nutrients in the agar and/or by low temperature. The nutrients for the growth of the BST are prepared separately and are either placed in a tablet or on a disc, with the tablet or disc placed on the solid agar medium containing the BST before carrying out a test. A test sample is then added and the sensitivity for sulfa drugs is increased by the addition of trimethoprin while an indicator is added either to the agar solution prior to solidification or to the nutrients so as to provide for increased sensitivity for sulfa drugs. However, sensitivity is not less than about 100–500 ppb.

It is desirable to provide for a microbial inhibition test kit, method and apparatus which is simple and effective to employ and is sufficiently sensitive to detect very low levels of drugs, particularly sulfamethazine in milk and other products.

SUMMARY OF THE INVENTION

The present invention relates to a test kit and method for the detection of drugs, and more particularly to a test kit, including a controlled heating and cooling apparatus, and method which is sensitive to sulfa and other drugs particularly at a level of less than about 50 ppb.

The present invention concerns a microbial inhibition test kit suitable for the screening of drugs at low concentration levels, particularly sulfa drugs, like sulfonamides and more particularly, sulfamethazine, for example, in various products, such as food products, and particularly milk and dairy products. The test kit comprises a first BST tablet containing a mixture which includes a thermophilic, spore-forming bacteria sensitive to the drugs to be tested, and more particularly *Bacillus stearothermophilus* (BST), the BST in a low, but effective amount and which BST is inhibited in growth by the presence of a drug in the sample. Typically, the first tablet is a low moisture-containing, compressed, BST-containing tablet which also contains a stabilizer for the BST spores in an inert filler-type material. The tablet contains a low moisture level, for example, less than 2 percent, and more particularly, less than 1 percent moisture and is compressed under such conditions so as to reduce any damage to the BST spores with generally compression being accomplished with a pressure for example of 5 to 10 newtons, for example, 3 to 4 newtons. The BST tablet generally contains a stabilizer for the BST spores, such as for example a carbohydrate, such as lactose, or an amino acid source, such as peptone, or more particularly, a combination thereof. The BST tablet usually contains a powdered, inert, water insoluble filler material to provide bulk for compression. Such a material may vary widely, but usually comprises for example a cellulose-type material such as an ethyl or propylcellulose or micro crystalline cellulose or celluloid powder. Compression of the BST tablet should take place under such time, temperature, pressure and friction conditions so as to prevent any substantial destruction of the BST spores in the tablet. The first BST tablet may also contain other ingredients, including a small amount of agar or other medium.

The test kit also includes a medium tablet which contains nutrients for the BST spores in the first BST tablet, the amount, type and concentration of nutrients present in the medium tablet are present sufficient to permit the detectable growth of the BST spores, but sufficiently low to provide low resistivity to the drug to be tested, so as to stress the BST during the test procedure and to provide for the detection of an antimicrobial drug, particularly such as a sulfanomide, to a detection concentration of less than about 50 ppb and as low as 0.5 to 20 ppb. The medium tablet containing the nutrients may comprise for example a portion of a nutrient broth at a level of for example 0.4 grams per liter or less, and more particularly carbohydrates as nutrients at a total amount of about 1.0 grams per liter or less. Suitable carbohydrates would include, but not be limited to: glucose; fructose; sucrose; and dextrose. Generally, amino acids may include, but not be limited to: tryptone, peptone and beef extract and similar products for example at a level of about 0.15 grams per liter or more particularly, 0.08 to 0.12 grams per liter.

Generally, the tablets include a buffer agent, such as alanine, and for example, a potassium or sodium phosphate buffer may be added to provide a pH of about 7.5. The tablets may include for example a salt, such as sodium chloride, as well as a non-ionic-type detergent, to enhance the sensitivity of the test. Further additives may include for example an antibiotic-free, non-fat dry milk where a test sample is derived from milk or a dairy product to reduce the variation in the test between test samples. The tablets also may include a thickening agent, such as a colloidal silica; a lubricant, such as a glycol, like polyethylene glycol; vitamin and phosphate sources. Other additives may include for example a calcium-chelating agent present in an amount to complex or chelate calcium in the test sample, such as ethylenediaminetetraacetic acid (EDTA) or ethylene glycol tetraacetic acid (EGTA) which additives are particularly effective in providing a sensitive test to tetracycline and tetracycline-type antibiotics, providing a sensitivity for example of 25 to 50 ppb or less. Other additives include antifoliate agents, such as trimethoprin (TMP) or methotrexate (MTX) or primethamine (PMA) to enhance the sensitivity of the test. The test results may be interpreted by the employment of a pH color indicator which can be based on an acid-base or redox or glucose monitoring and particularly where a pH color indicator is used, may comprise bromocresol purple or phenol red or a redox color indicator. Usually, the pH color indicator is added to the medium tablet while the calcium chelating or antifoliate agents and buffers are usually added to the medium tablet.

The test kit also includes a test container, such as for example a multiwell plate, a test tube in which the BST tablet, the medium tablet and test sample may be introduced, heated, cooled and incubated so as to permit the rapid and efficient assay screening of drugs by the absence of change or change in color of the pH indicator included or by monitoring the glucose.

The test method is directed to a test for the determination of drugs, such as sulfa drugs and other antimicrobial drugs, in a test sample at a defined, low concentration level, particularly at concentration levels where sulfamethazine and sulfa drugs are below about 50 ppb. The test method comprises placing a defined amount of a test sample into a test container and heating the sample to a temperature sufficiently high to destroy the natural inhibitors in the sample, and thereby enhancing the further sensitivity of the test, such as for example, heating a test sample derived from raw or pasteurized milk to a temperature of about 100° C. for about one to five minutes. The test method includes cooling the heated sample to a defined lower temperature, for example, to a temperature of less than about 85° C. and more particularly, about 80° C. to 85° C. The test method then includes adding the BST-containing tablet to the cooled test sample, the tablet comprising a low moisture-containing, compressed tablet of the BST spores, a stabilizer and an inert bulking and filler material. Thereafter, the test container with the BST spores and the sample are rapidly heated to a defined temperature to heat shock the BST spores so as to affect generally synchronous germination of the BST spores. Generally, the rapid heating of the BST spores in the test sample is done to a temperature of about 100° C. or more for about 0.1 to 2 minutes. Antifoliate agents such as TMP tend to be destroyed on heating; therefore, TMP is typically added to both the BST tablet and the medium tablets to insure the presence of TMP in the test to enhance sensitivity particularly for sulfa drugs.

The test method includes adding a medium tablet containing the nutrients to the heat-shocked BST spores and test sample in the container. A medium tablet comprising nutrients merely sufficient for the growth of the BST spores, but sufficiently low to provide for low resistivity to the drug to be tested so that the test is particularly sensitive. The test container containing the test sample, BST and medium with the nutrients are then incubated, for example, at an incubation temperature of 65° C. ±1° C. and incubation time for about 2 hours 45 minutes to 3 hours 15 minutes. The test method includes terminating the incubation at the defined end of the incubation period, either by removing the test sample from the incubator or by rapidly increasing the incubating temperature to over about 75° C. for a time period to terminate further growth of the BST. Thereafter, the presence or absence of the drug in the sample within a defined concentration level is detected, particularly simply by observing the absence or change of color of the pH color indicator included or by glucose monitoring or a redox indicator. A sulfa drug, particularly a sulfamethazine, present in an amount of less than 20 ppb will test positive. The sensitivity may be as low to sulfa drugs like sulfamethazine, as low as 10 ppb or lower, thereby providing for an extremely sensitive test kit and method for hitherto available to possible.

The test kit and method permits the sensitive determination of antimicrobial drugs in a wide variety of materials, particularly in food products and body fluids, for example, but not limited to: raw and pasteurized milk; urine; and other body fluids; and meat. Generally, test samples taken from the material to be tested are placed in liquid form and a defined volume of liquid may be optionally added to the test container, while the tested material placed in liquid form and liquid aliquots taken. The test kit and method are sensitive for example to 0.5 to 20 ppb levels of sulfonamides depending on the individual sulfa drugs tested. The test kit and method also have excellent sensitivity to aminoglycocides, especially to gentamicin to a level of about 30 to 80 ppb and neomycin to a level of about 100 ppb or less. The assay may be performed in any test container, such as test tube or a plate and incubated in a heat block or water shaker bath.

The test method may be carried out in an automatic system and apparatus wherein preheating, cooling, heat activation and incubation are controlled in a single, automated system and apparatus. The test kit may include a control apparatus which comprises a metal heating block, such as for example, made of aluminum, having at least one and typically a plurality of openings therein to form and arrange for the insertion of a test container, more generally a test tube, to be heated with electrical means, e.g. coils in the block, to heat the metal block so that the test tube and the test sample will be rapidly heated to defined temperatures as required in the test method. The test apparatus also includes a separate metal cooling block, typically of aluminum, and generally of defined and greater mass than the heating block to provide for the rapid cooling of the heating block when placed in contact therewith to the defined cooled temperature as required in the test method. Generally, the heating and cooling blocks are placed in a spaced apart heating position when the heating of the sample containers are required and are placed in an adjacent, contacting, heat exchange cooling position when cooling of the sample containers are required. The heating and cooling blocks are moved between positions by tilting the control apparatus to provide for slidable movement of the blocks. The incubation is done in the tilted position to enhance the oxygen transfer rate. The test apparatus also includes electrical circuitry and control programming means based in the test method to provide for the sequential timed heating of the heating block and to signal the time period for the movement of the heating and cooling blocks between heating and cooling positions and to provide signal means, e.g. lights or audible means, for the termination of the various test steps and the termination of the incubation and termination of the test sequence. While the control apparatus is useful in the test method, the control apparatus may be usefully employed where rapid heating and cooling of test samples at defined test times are of importance.

The test kit and method have significant advantages over prior art inhibition, disc-type tests in that the test kit and method do not require the employment of agar or an agar-type support. The use of a separate BST tablet and a medium tablet provides for a long shelf life, typically of at least a year, and where storage may be accomplished at ambient temperatures, such as 60° F. to 70° F. In contrast, the prior art test method requires a solid agar medium with the BST which has a limited shelf life of not more than about three to six months and which medium must be stored at refrigerated temperatures of 40° F. The test kit and method are also more sensitive than the prior art test. The test kit and method do not require the employment of a paper disc or the reading of the test sample by visual examination of a zone of inhibition around the periphery of the disc. Therefore, the test kit and method represent a significant advance, both in simplicity, convenience, shelf life and sensitivity in the determination of antimicrobial drugs.

The test kit and method have been described as employing separate BST and medium tablets; however, it is recognized that a single tablet may be prepared and used rather than separate tablets provided that the single tablet or composition preparation prevents the growth of the BST in the tablet in the presence of the nutrients, such as for example by segregating, coating or otherwise treating the BST spores or the nutrients to prevent interaction and provide for long shelf life.

The test kit, including the control apparatus, and method provide a simple, antimicrobial drug screening test. The test is sensitive to beta lactams, tetracycline, sulfa drugs, amino glycocides and macrolides concentration levels as follows, with the following concentration range in ppb per minimum positive color:

| | |
|---|---|
| Penicillin | 2.4 to 3.6 |
| Sulfamethazine | 15–20 |
| Sulfadimethoxine | 8–10 |
| Gentamicin | 30–80 |
| Oxytetracycline | 80–100 |
| Tylosin | 40–60 |

The test kit and method are a qualitative test kit and method intended for determining antimicrobial drugs, particularly for raw and pasteurized milk testing. The tablets in the test kit may still have a shelf life at room temperature at 20° C. to 25° C. for up to one year. The test kit and method develop in approximately 2 hours and 55 minutes. The test kit may also contain for example microbial tablets in a blister pack for example of 20, medium tablets in blister packs for example of 20, negative control tablets in blister packs of 2, a pipet, water, pipet tips and test tubes. The equipment employed include an automatic test block to carry out the test sequence, test tube caps which are reusable, a 0.2 ml pipet and a marker pen.

The ingredients and additives as described for use in the BST and medium tablets may vary as desired and may be adjusted in order to provide for particularly sensitive detection of particular drugs. Typically, the BST spores should not be used in excess, but sufficient to permit growth and to provide for detection of the antimicrobial drug, and generally are employed for example in the amount of $10^6$ to $10^7$ spores per tablet.

The test kit, method and apparatus of the invention will be described for the purposes of illustration only in connection with certain preferred, illustrated embodiments; however, it is recognized that various changes, modifications, additions and improvements may be made to the test kit, method and apparatus by those persons skilled in the art without departing from the spirit and scope of the invention.

DESCRIPTION OF THE EMBODIMENTS

Figure 1:
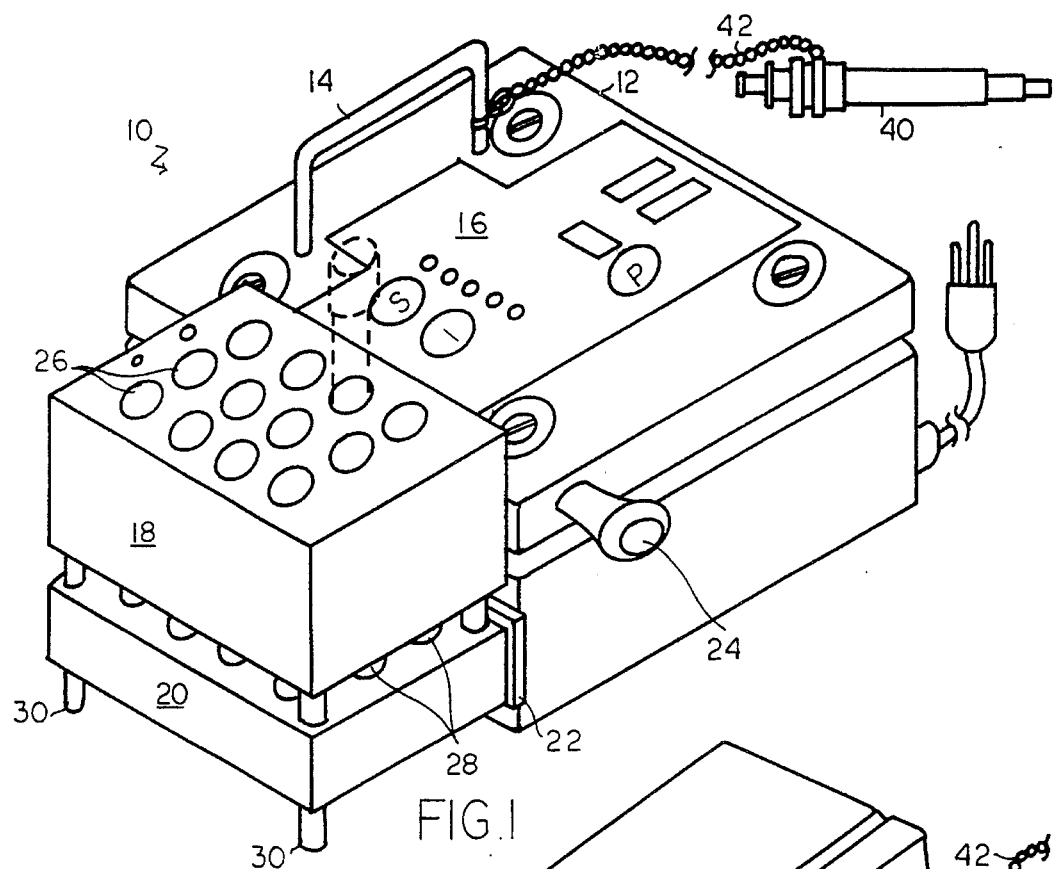
FIG. 1 is a perspective illustrative view from above of a test apparatus for carrying out the test method of the invention showing the test apparatus in a heating position.
Figure 2:
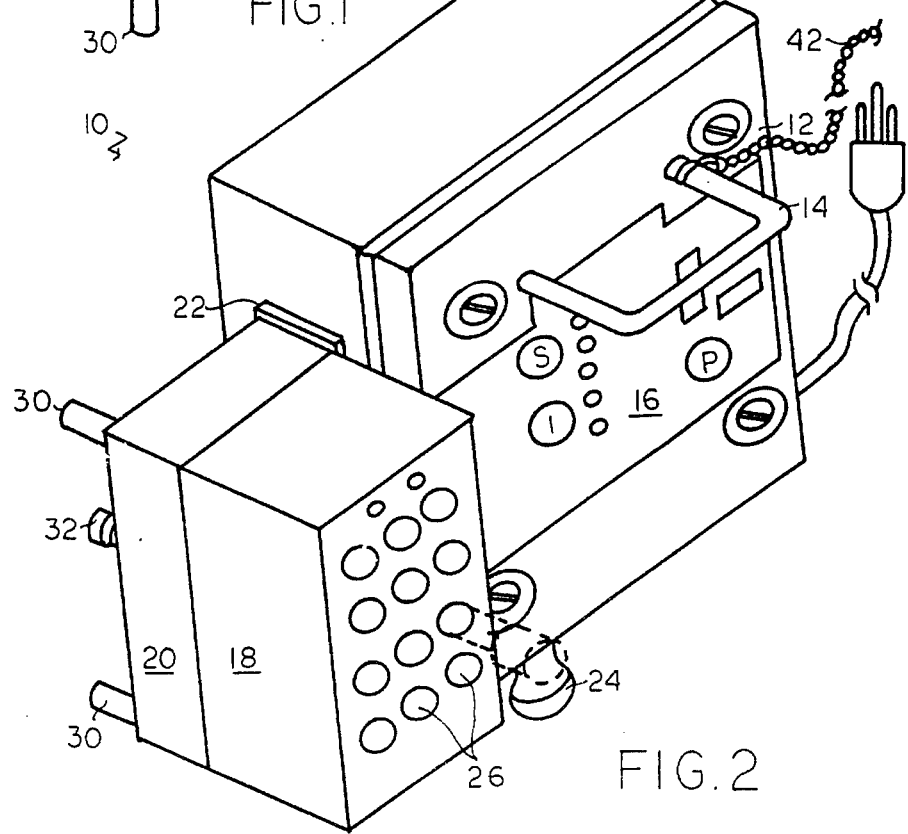
FIG. 2 is a perspective, illustrative view from above of the test apparatus of FIG. 1 showing the test apparatus in a tilted position for cooling and incubation.

Compressed, low moisture BST and medium tablets were prepared with the following composition:

| | Ingredients | BST Tablet | Medium Tablet |
|---|---|---|---|
| 1. | Microcrystalline cellulose (tablet bulking agent and binder) | 22.6 mg | 25.5 mg |
| 2. | Sodium chloride (isotonic agent) | 1.6 mg | 1.6 mg |
| 3. | Polyethylene glycol (PEG) (lubricant) | 600.0 ug | 600.0 ug |
| 4. | [a]Powdered milk — skimmed, dried, antibiotic-free (general supplement and nutrient) | 953.0 ug | 953.0 ug |
| 5. | Tryptone (amino acid supplement) | 100.0 ug | 100.0 ug |
| 6. | Alamine (amino acid supplement and buffer) | 100.0 ug | 100.0 ug |
| 7. | Potassium phosphate (buffering agent and phosphate source) | 76.0 ug | 76.0 ug |
| 8. | [b]Peptone (amino acid source) | 12.6 ug | 12.6 ug |
| 9. | Bromocresol purple (pH indicator) | 15.0 ug | 15.0 ug |
| 10. | Colloidal silica (stabilizer and thickener) | 8.3 ug | 8.3 ug |
| 11. | Beef extract (vitamin source) | 0.74 ug | 0.74 ug |
| 12. | [d]Trimethoprin (optional folic acid analog-sensitizer) | 29.2 μg | 29.2 μg |
| 13. | Non-ionic surfactant (to increase penetration of BST spores) | 0.15 ug | 0.15 ug |
| 14. | EGTA-chelating agent Tween-80 | 142.7 ug | 142.7 ug |
| 15. | [c]BST spores | 2.90 ug | -0- |
| 16. | Glucose | 500 μg | 500 μg |

[a]The powdered milk may be substituted by other materials where the test is designed to test other samples, such as urine or blood. The presence of the antibiotic-free test sample materials aids in eliminating differences between test samples.

[a] The powdered milk may be substituted by other materials where the test is designed to test other samples, such as urine or blood. The presence of the antibiotic-free test sample materials aids in eliminating differences between test samples.

[b] In the above example, the amino acid source is split between the tablets; however, 5% to 20% of the amino acid source may be placed in the BST tablet and the rest in the medium tablet. The total amino acid source is fixed to stress the BST to increase sensitivity.

[c] The BST spores may vary in concentration, but never exceed $10^7$/ml.

[d] To increase sensitivity for sulfa drugs. The above tablets have a long shelf life and need not be refrigerated, but stored at room temperature, 20° C. to 25° C., for up to one year.

The above BST and medium tablets used in a test tube as the test container with a liquid sample, such as milk, provide enhanced antimicrobial drug sensitivity in the described test method, as follows:

MINIMAL DETECTION LEVELS

| Antibiotic | Prior Art | Invention |
|---|---|---|
| BETA-LACTAMS | | |
| Cephalexin | 50 | 50 |
| Oxacillin | — | 8 |
| Hetacillin | 8 | 10 |
| Penicillin (various) | 2 | 3 |
| Cephapirin | 8 | 10 |
| Cloxacillin | 20 | 30 |
| Ceftiofur | 50 | 40 |
| Ampicillin | 4 | 4 |
| Cefalonium | | |
| Cefadroxil | | |
| Amoxicillin | | |
| SULFONAMIDES | | |
| Sulfamethoxazole | — | 5 |
| Sulfaquinoxaline | — | 8 |
| Sulfamethizole | 100 | 10 |
| Sulfisoxazole | 100 | 8 |
| Sulfadimethoxine | 100 | 8 |
| Sulfapyridine | 250 | 20 |
| Sulfamethazine | 500 | 15 |
| Sulfadiazine | 250 | 20 |
| Sulfachloropyridazine | — | 5 |
| Sulfamerazine | — | 20 |
| Sulfathiazole | 100 | 10 |
| Dapsone | — | 0.5 |
| Sulfacetamide | — | 50 |
| Sulfanilamide | 1000 | 50 |
| Sulfadoxine | — | 5 |
| AMINOGLYCOSIDES | | |
| Streptomycin | 4000 | 600 |
| Kanamicin | 10000 | 1500 |
| Gentamicin | 250 | 50 |
| Neomycin | 1000 | 75 |
| MACROLIDES | | |
| Erythromycin | 400 | 200 |
| Tylosin | 100 | 40 |
| TETRACYCLINES | | |
| Tetracycline | 200 | 50 |
| Chlorotetracycline | 500 | 150 |
| Oxytetracycline | 200 | 80 |
| OTHERS | | |
| Novobiocin | 500 | 600 |

The test kit and method provides for nutrients and bacteria or BST spores stabilized in dry, compressed tablets (separately or together) which are introduced into a liquid sample. The test method in the liquid phase does not require any agar or diffusion barrier, thus better contact of inhibitors and BST spores or bacteria is achieved. The test method may use test tubes and multiwell plates and be incubated in the standard form heat block/water bath or employing the control test apparatus. The composition of the tablets and test method, e.g. heating times, may vary to provide for select sensitivity to particular antimicrobial drugs, such as the variation in BST spore concentration. As illustrated, a pH color change indicator usually shows the test results with a yellow color indicating a negative test, and a blue color indicating a positive test e.g. sulfa drug present at a concentration level of greater than 10 ppb.

The microbial inhibition test method may be carried out without the use of the control special heating incubator-cooling test apparatus. The test method provides a single screening test based on color change with the test results for all members of an antimicrobial drug family. For example, in the described tablets, the concentration range (ppb) for a minimum positive (blue) color would be: penicillin, 2.4–3.6; sulfamethazine, 15–20; sulfadimethoxine, 8–10; gentamicin, 30–80; and tetracycline, 30–80.

The test kit may comprise a plurality of separate BST and medium tablets generally in a blister package form and one or more negative control tablets and requires distilled water. The equipment required includes a fixed pipet, e.g. 0.2, and disposable pipet tips, test tubes or multiwell plates, dropper or drop dispenser, 66° C. shaker water bath with test tube rack and hot plate to boil water to timer. Then the test kit includes the control apparatus, the water bath, test tube rack and hot plate are not required.

For example, for testing a large number of samples, the test is conducted as follows:

1. Label test tubes (13×100 mm) and place in rack.
2. Add 0.6 ml distilled water into each test tube.
3. Add 0.2 ml of milk sample into test tube and mix well. Use new tip for each sample.
4. Heat test tubes in boiling water for 6 minutes. Remove test tubes to table top to cool.
5. Add one microbial tablet to each test tube by pushing the tablet through the blister into the test tube with the blunt end of a pencil.
6. Place test tube back in boiling water for 2 minutes. Remove immediately after 2 minutes.
7. Let cool to the touch (tap water may be used to hasten cooling) and add one medium tablet to each test tube.
8. Cap test tubes with the plastic caps and place in 66° C. ±1° C. shaker water bath. Set shaker at 100 rpm.
9. Start timer for incubation time specified on each kit, e.g. 3 hours.
10. When time is up, remove test tubes from incubator.
11. Observe color change. Blue indicates positive; yellow-green is negative.

Color can be stabilized for up to 24 hours by placing test tubes in boiling water for 2 minutes.

Figure 8:
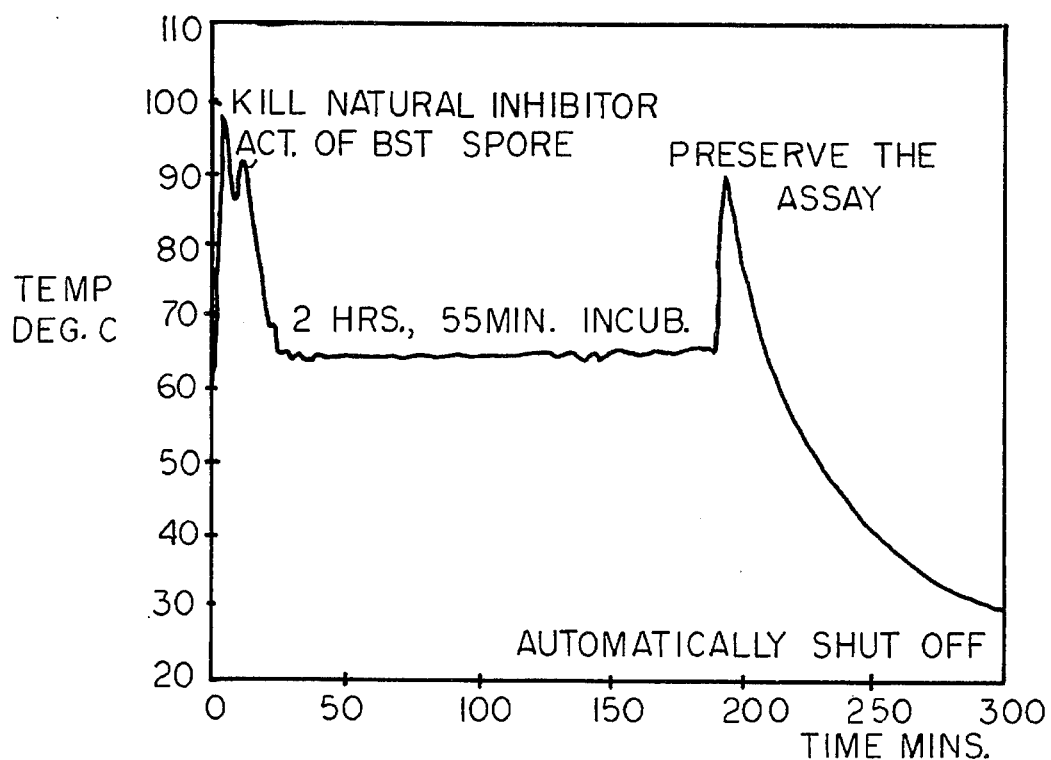
FIG. 8 is a graphical illustration of a test method employing the test apparatus showing the temperature in degrees Centigrade (Temperature Deg C) versus the time in minutes (Time Mins) of a test sample.
Figure 9:
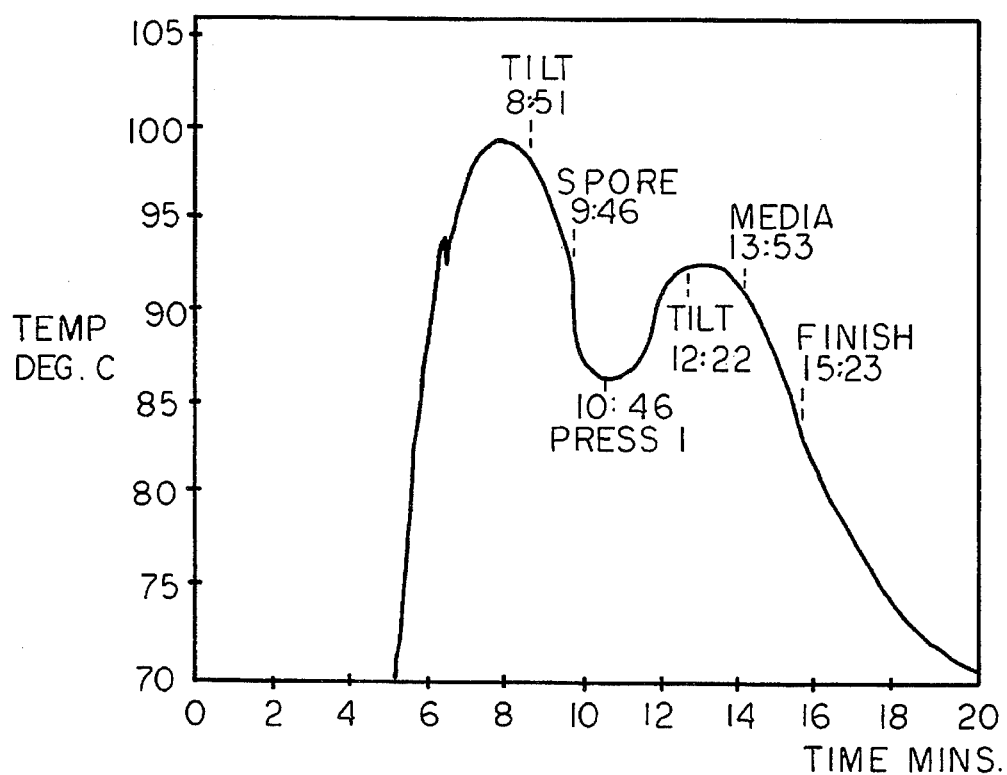
FIG. 9 is an enlarged graphical illustration of a portion of the test method shown in FIG. 8.

The time-temperature profiles will be the same or similar to those graphical profiles of a test shown in FIGS. 8 and 9 of the drawings.

The test method may be carried out particularly for a continually and large number of test samples employing a control test apparatus as illustrated particularly in FIGS. 1–5 of the drawings. The test apparatus is a combined automatic heating incubator and cooler with circuitry and programming to provide for the signal and timed sequence of the test steps for ease of use of the test user. The apparatus 10 comprises a control housing 12 including a power supply (see FIG. 7) and electrical circuitry (see FIG. 6) with a raised handle 14 and a control panel 16 on the top surface and a short support leg 24 on one side of the housing 12, the handle 14 permitting the user to tilt the apparatus 10 to a tilt position, for example, about 75° from horizontal and to rest the housing on support leg 24 in the tilt position. The apparatus includes a solid, slidable aluminum cooling block 18 with a plurality of uniformly disposed holes 26 passing therethrough for the insertion of test tubes 36 containing the test samples to be incubated. The apparatus 10 includes a solid dimension heating block 20 secured to the one side of the apparatus 10 and heat insulated therefrom by a layer of rubber-foam insulating material 22. The heating block 20 also has a plurality of uniformly distributed holes 26 therein aligned with holes 28 of the cooling block 18 to receive and retain the bottom portion of the test tubes 36. The cooling block 18 is designed of sufficient mass to provide for the desired rapid cooling of the heating block 20 and retained test tubes 36, while the heating block 20 has electrical heating coils (see FIG. 6) to provide for the heating-incubation of the test tubes 36 with the test samples. The test tubes 36 are illustrated in dotted lines in FIG. 1 and 2 and shown with sealed caps in FIG. 3 and 4. The heating block 20 includes legs 30 to support the one side of the block 20. The cooling block 18 includes a central, fixed length rod 32 secured to the cooling block 18 and extending through a hole (not shown) in heating block 20 and designed to support the cooling block 18 in a spaced apart, non-cooling position above the heating block 20 when apparatus 10 is in a generally horizontal position (see FIGS. 1 and 4), the bottom portion of the rod 32 resting on the table support-like legs 30. When the apparatus 10 is placed in a cooling position, the apparatus 10 is tilted to rest on support 24 (see FIG. 2 and 4) through the use of handle 14, so that the tilt permits the lower surface of the cooling block 18 now unsupported by rod 32 to slide into direct heat exchange contact with the top surface of heating block 20 (the heating or incubating then finished) and to permit rapid cooling of the block 20 and the retained test tubes 36 with the liquid samples 38. The tilt position is also designed to expose the maximum top surface of the liquid test sample 36 in the tilt position to expose the maximum surface of the test sample 38 to the air (see FIG. 4). The test apparatus optionally may include an Eppendorf fixed pipet 40 secured by chain or cable 52 to a screw on the housing (see FIG. 1; not shown in FIGS. 2–4). The control apparatus provides for automatic, preset, pre-heating, cooling, incubation and fixation of test results (tilt position).

Figure 3:
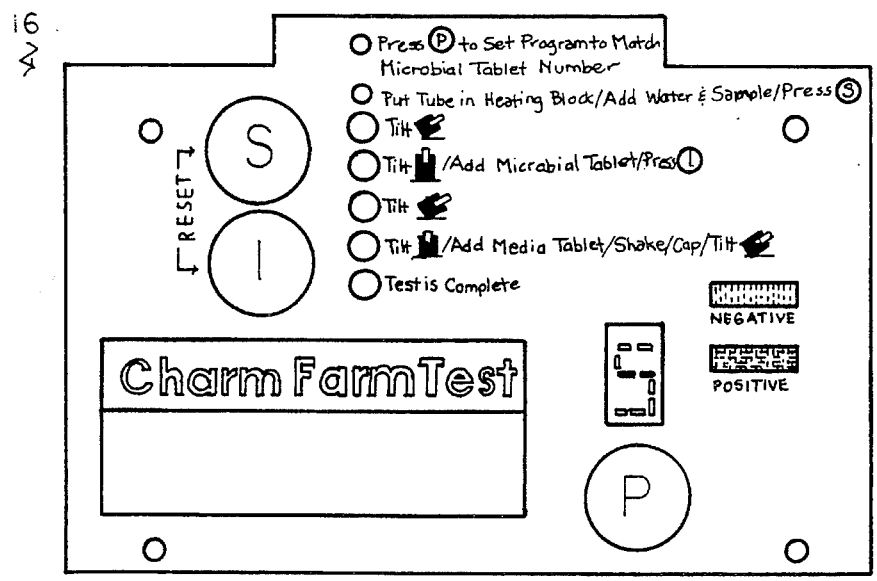
FIG. 3 is an illustration of the front control panel of the test apparatus of FIG. 1.
Figure 4:
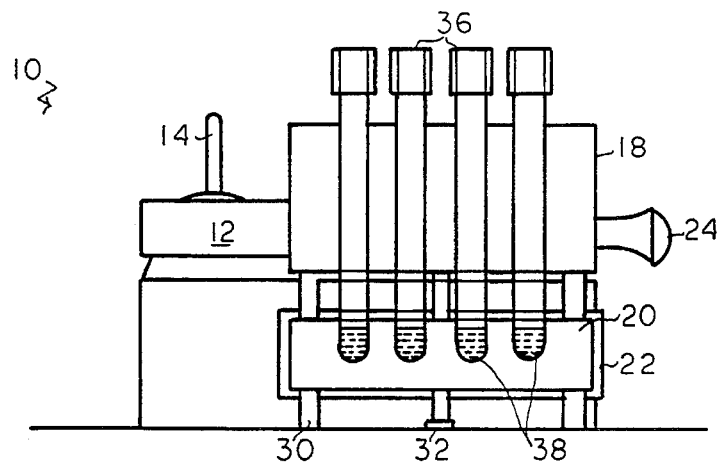
FIG. 4 is an illustrative, partially sectional side plan view of the apparatus of FIG. 1
Figure 5:
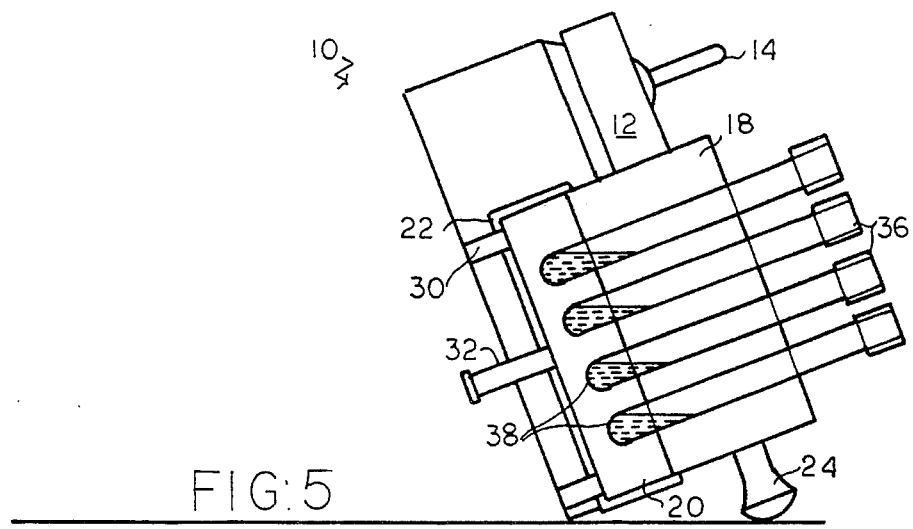
FIG. 5 is an illustrative, partially sectional side plan view of the test apparatus of FIG. 2.

The control panel 16 of apparatus 10 is shown more particularly in FIG. 3 and includes a start button S to start the automatic test cycles when the test tube 36 with sample 38 is inserted in holes 26 and 28. The panel includes aligned signal lights 44 with printed instructions opposite each light, the lights operating to signal action in the test method by the user. The panel 16 includes comparative negative and positive color indicators 46 so the test results can be compared with standard indicator colors. The test program can be reset by pressing buttons I and S together. Button I controls the start of the selected incubation period. The panel includes program button P with a digital LED readout 48. The user sets the proper program (time of incubation, etc.) by pushing button P to display a number according to the number on the microbial tablet, for example, numbers 1 to 9, with the tablet varied in concentration and ingredients for the detection of particular antimicrobial drugs to a selected sensitivity, and the program selected designed for particular matrices, such as milk, serum, urine, meat and eggs. For example, the number 5 as illustrated in display 48 is for fixed incubation time of 2:55 minutes with lower program numbers of lesser incubation time and higher program numbers of greater incubation time for a variation of ±25–30 minutes in incubation time permitted to the user by the program P button.

Figure 6:
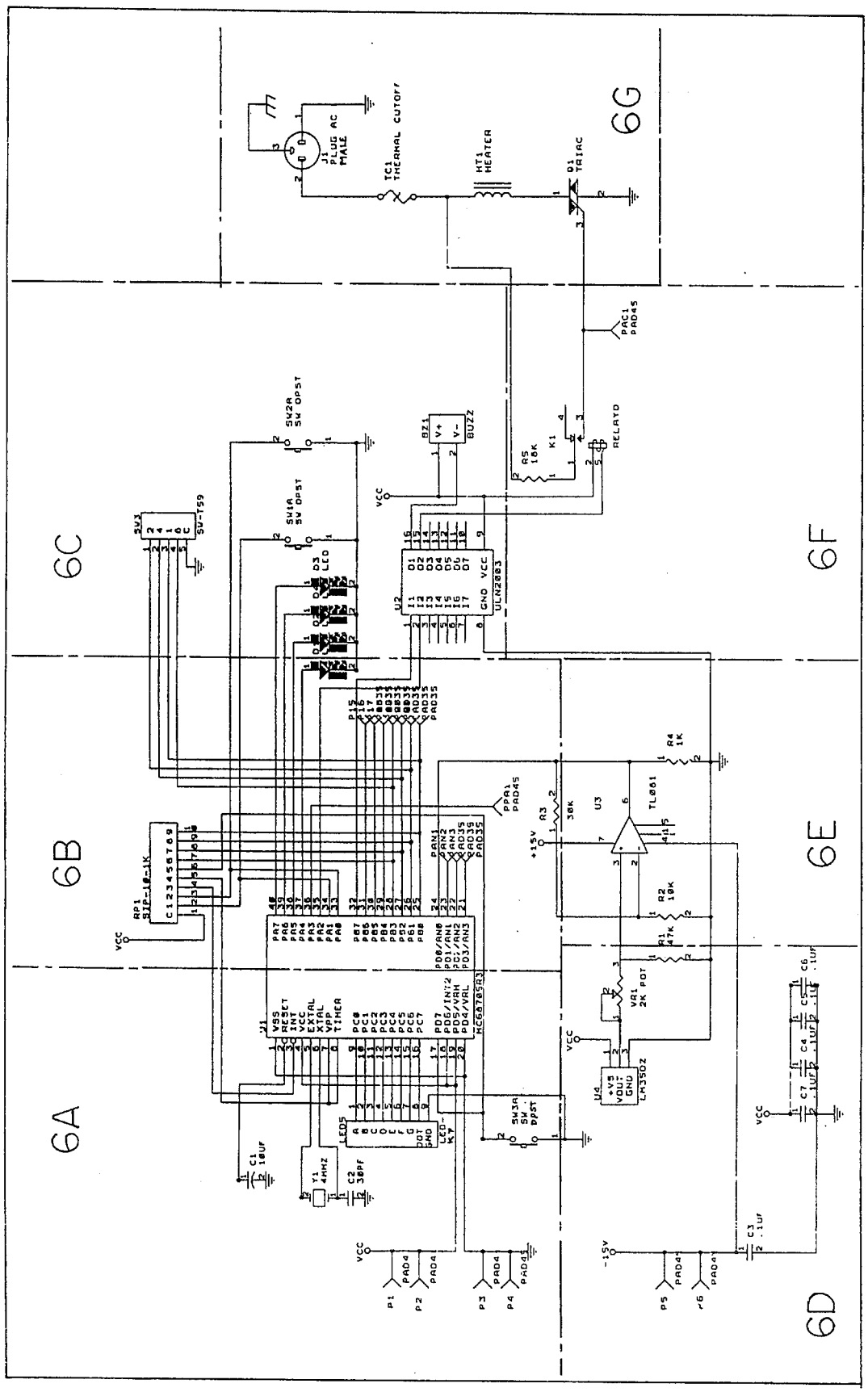
FIG. 6 is an illustrated electrical circuitry and programming diagram of the test apparatus.
Figure 6A:
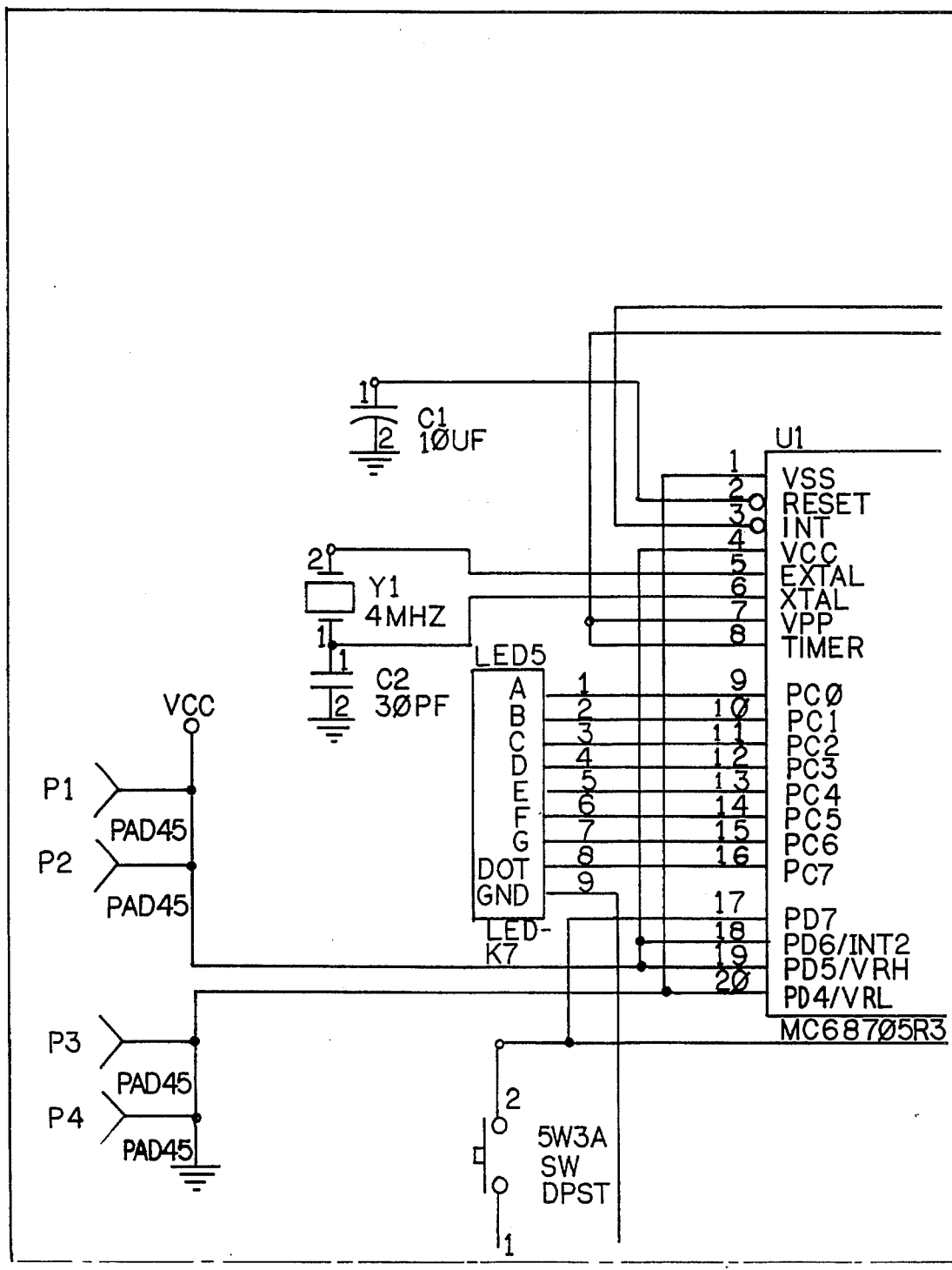
Figure 6B:
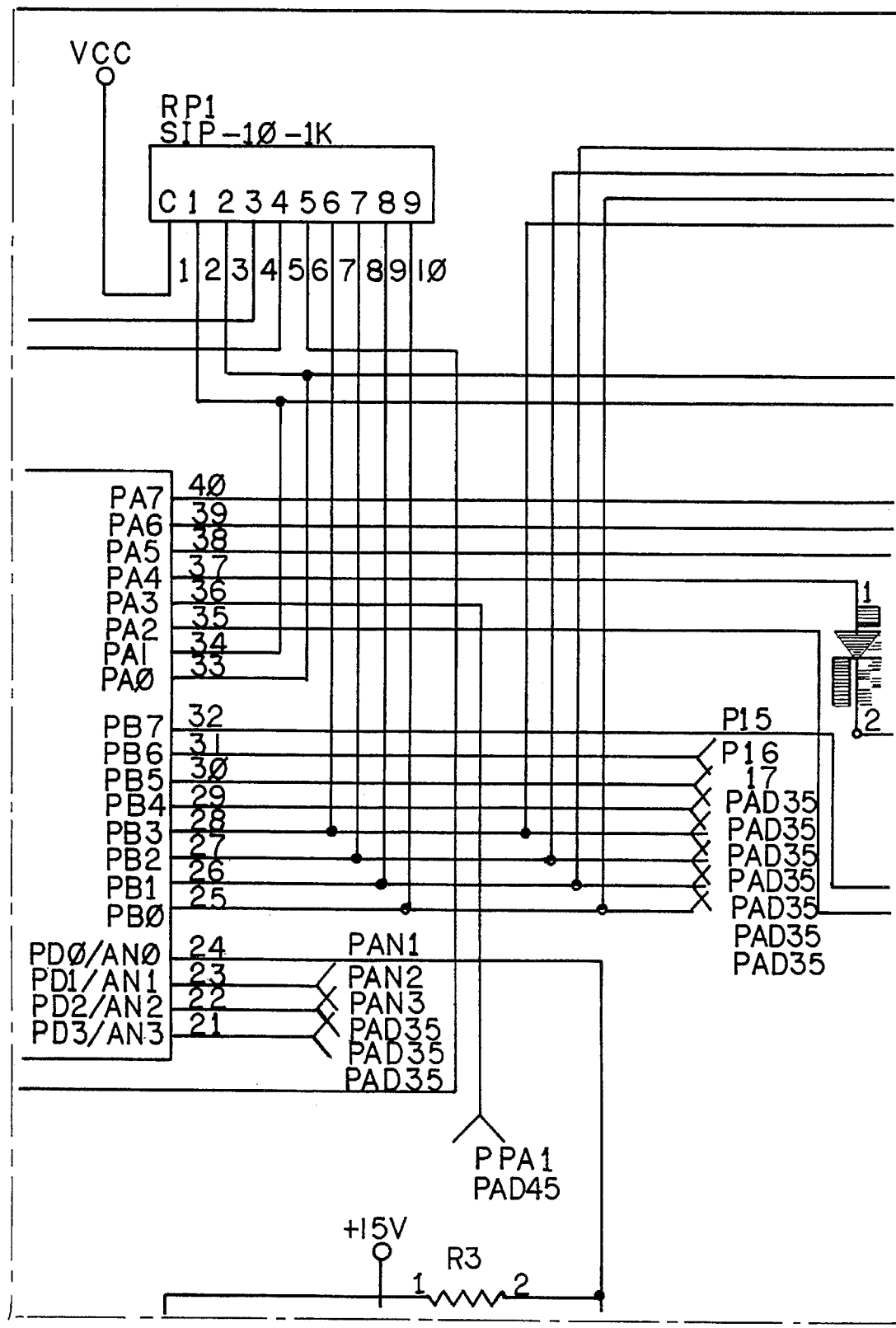
Figure 6C:
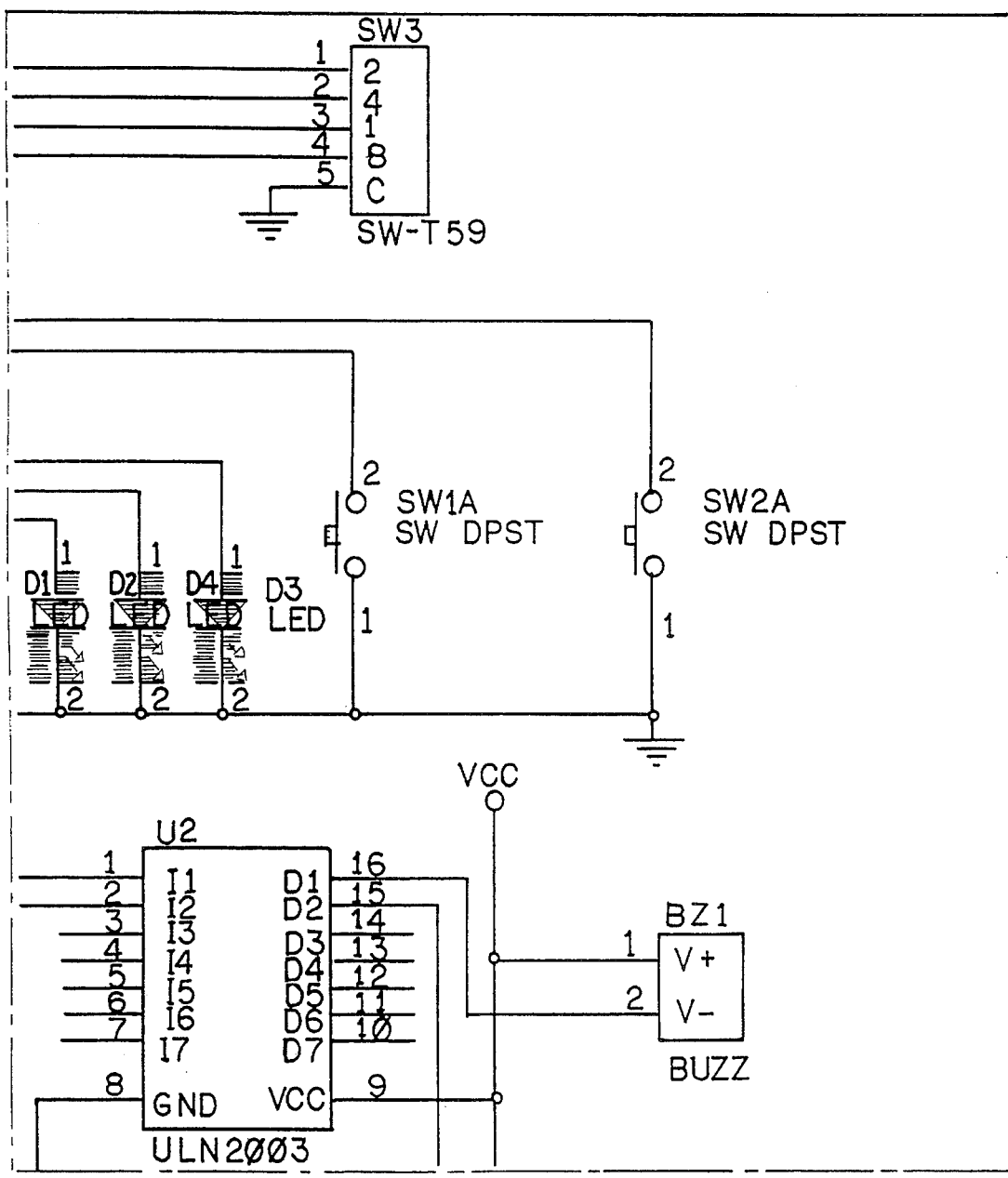
Figure 6D:
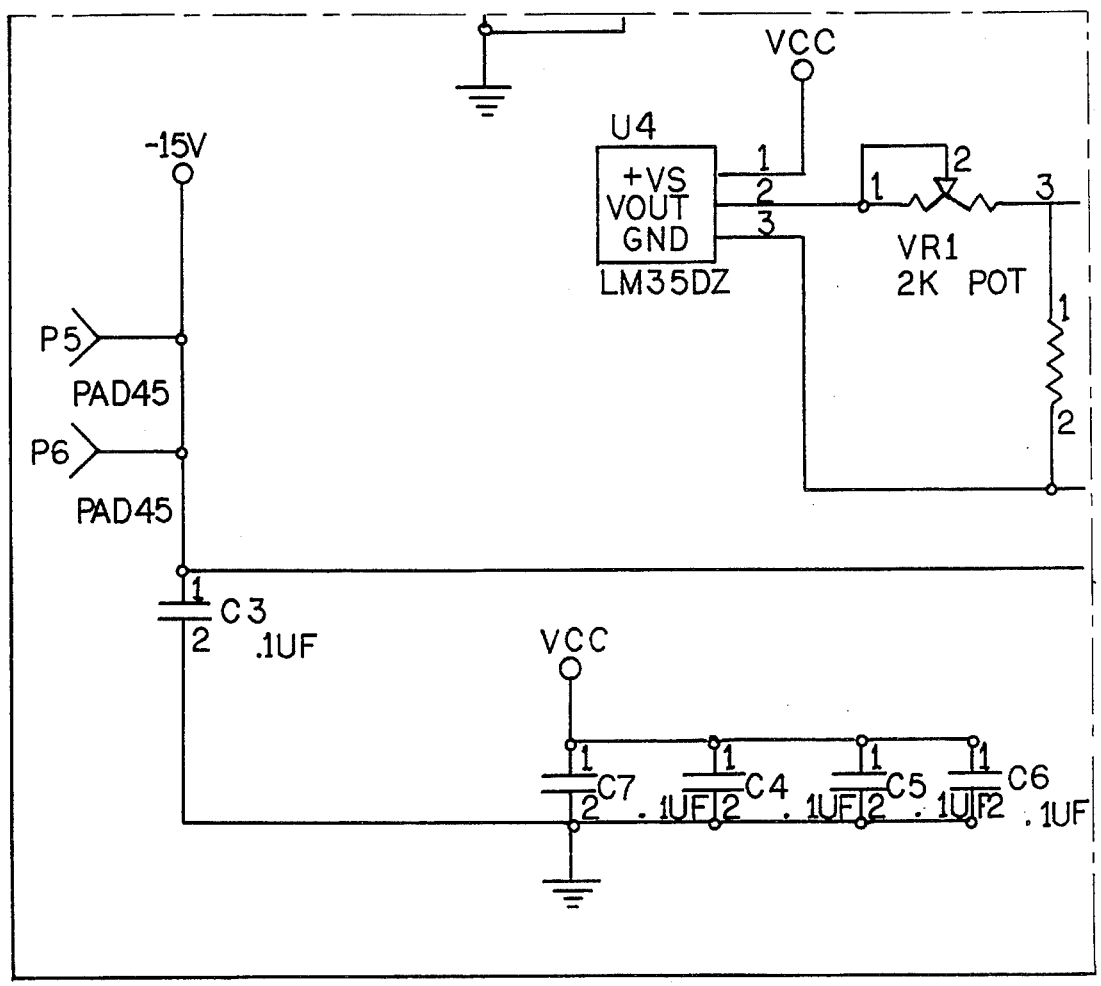
Figure 6E:
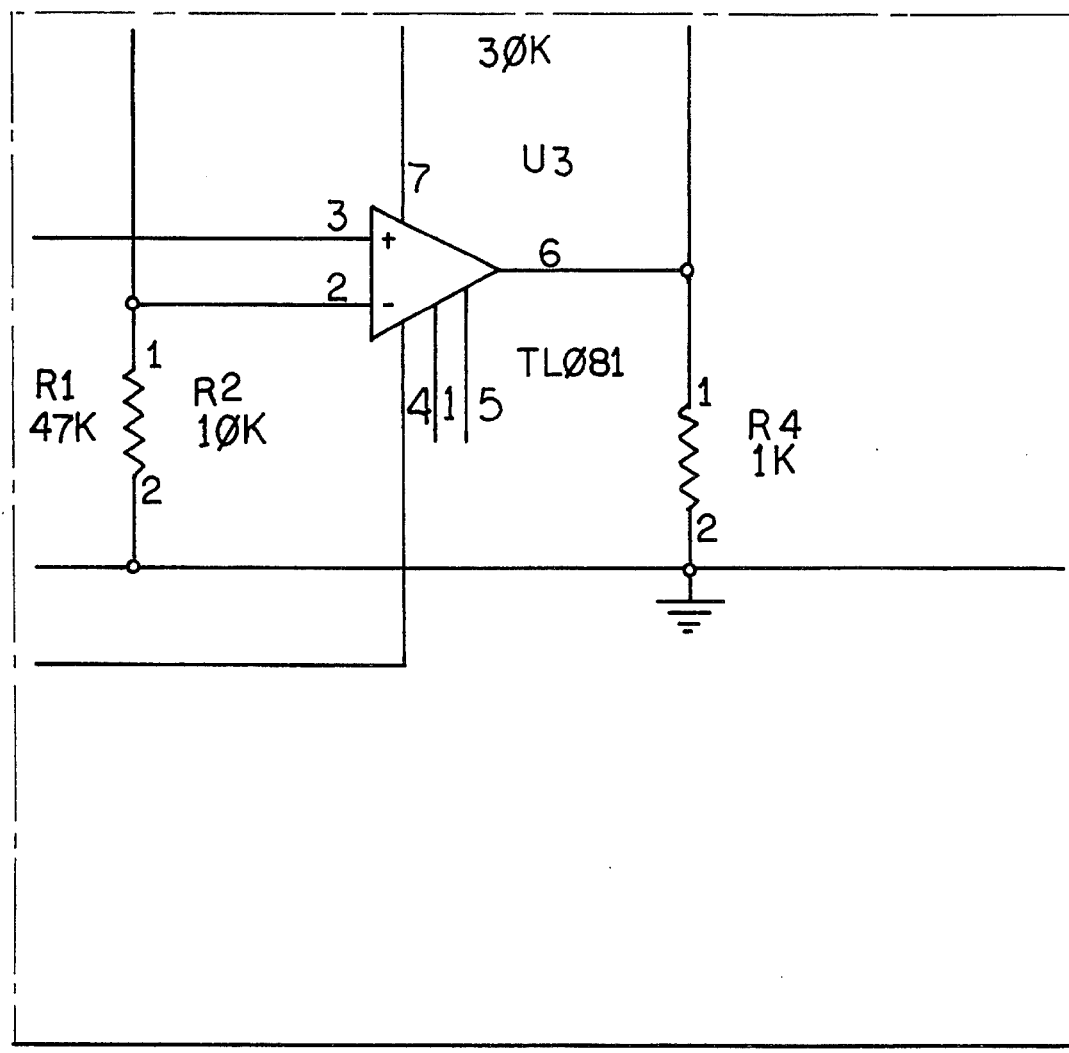
Figure 6F:
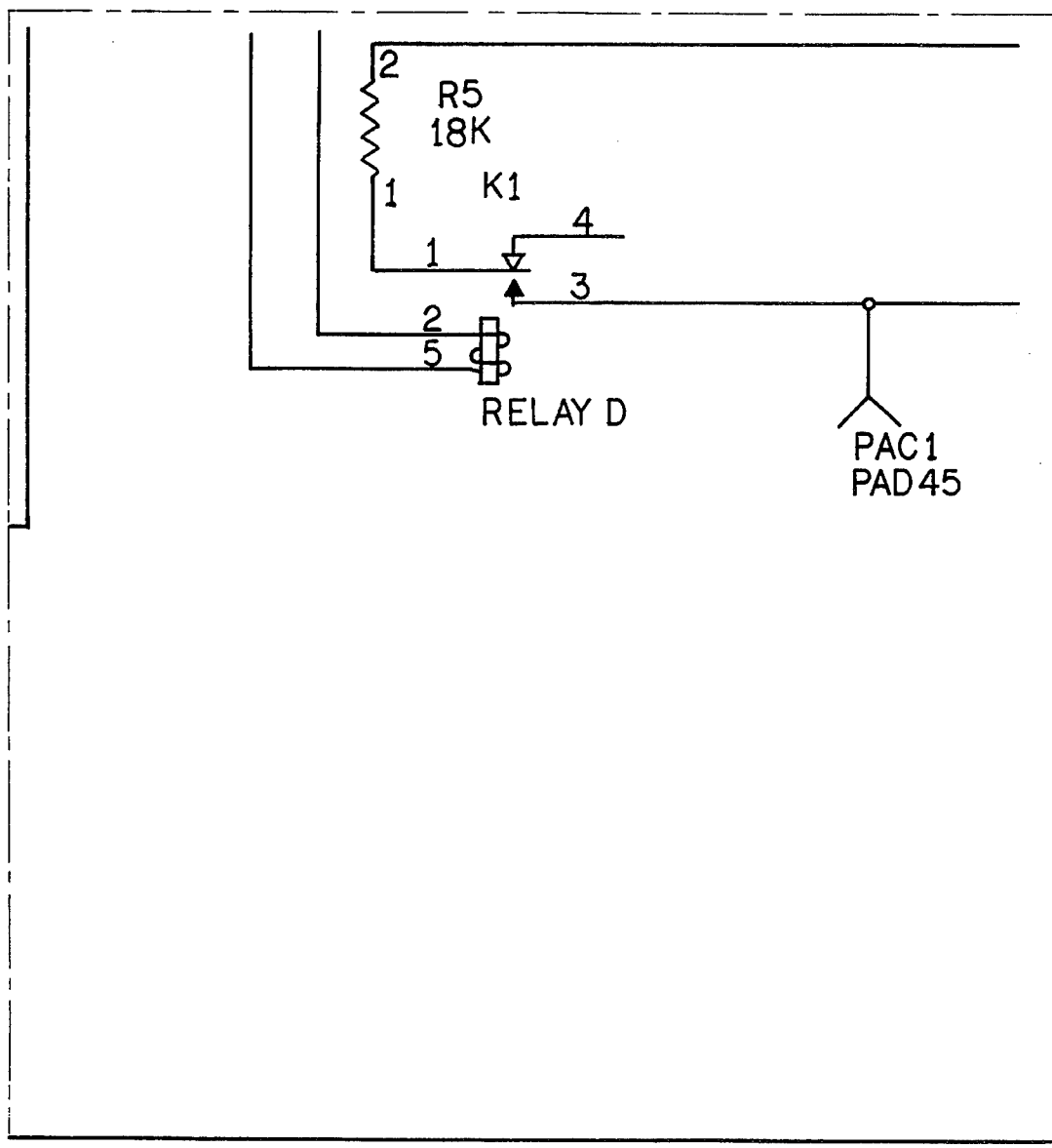
Figure 6G:
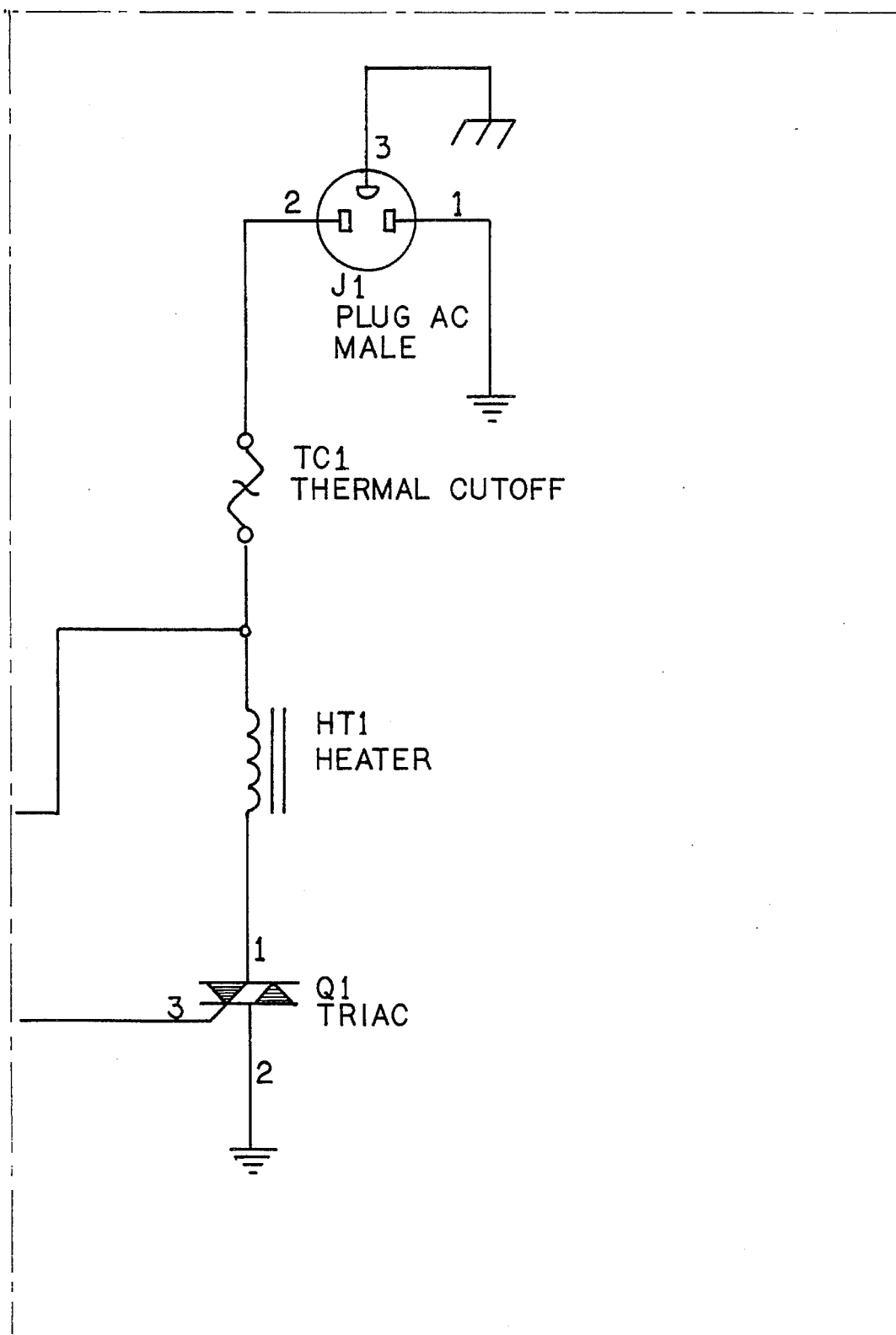
Figure 7:
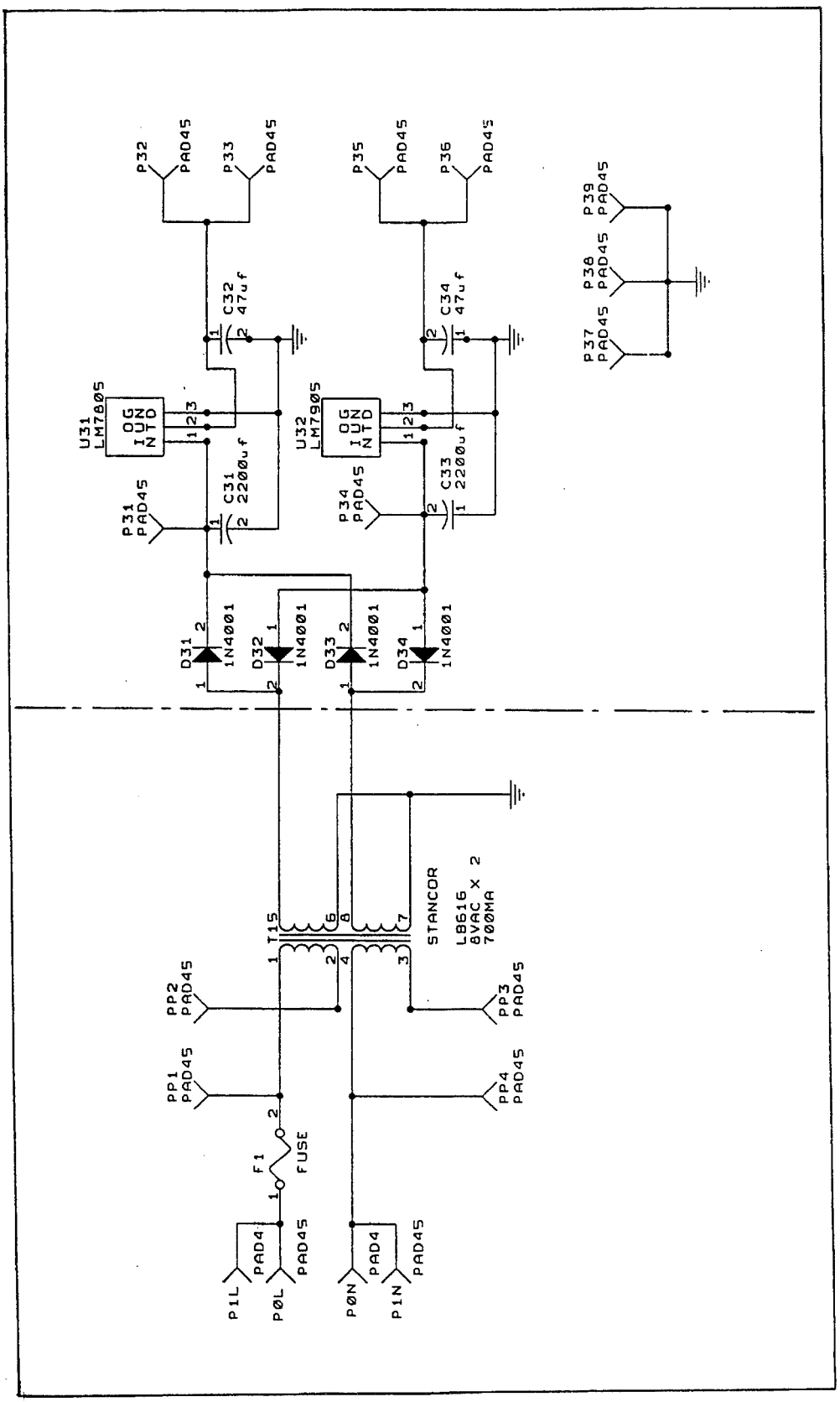
FIG. 7 is an illustrated electrical circuitry diagram of the electrical power supply used in FIG. 6.
Figure 7A:
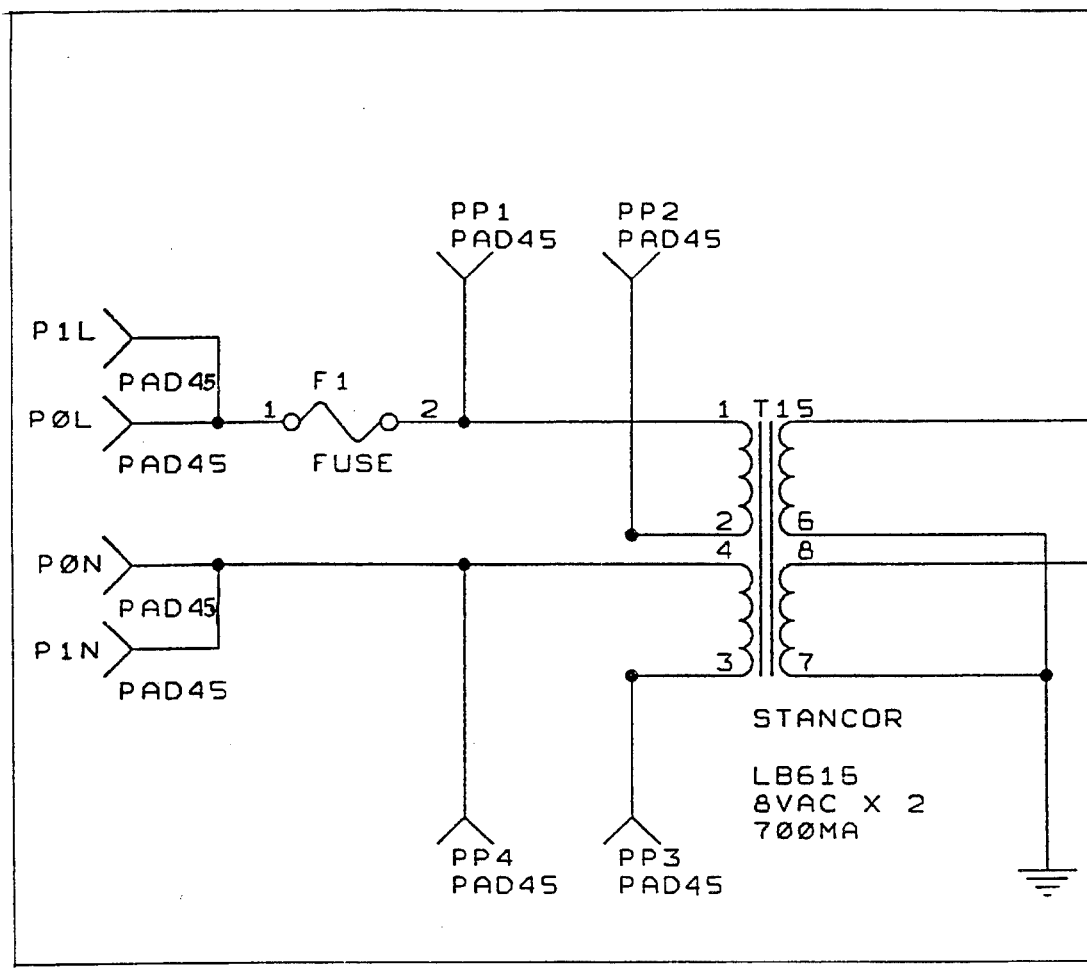
Figure 7B:
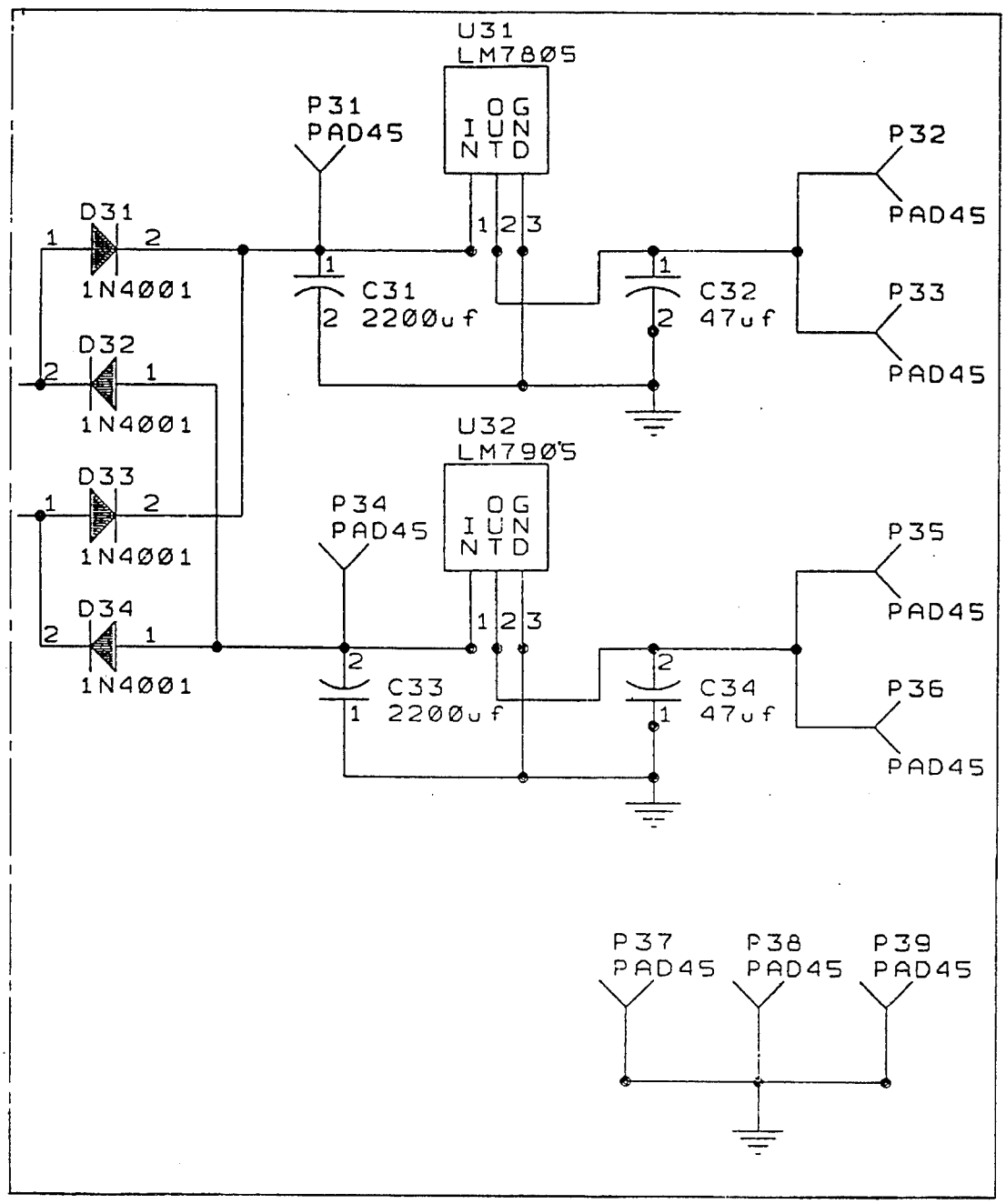

FIG. 6 shows the program circuitry of the test apparatus 10, while FIG. 7 shows the power supply circuitry.

The test method for the test apparatus in the determination of 10 ppb or less of sulfa drugs in milk samples is as follows:

1. Press S and I buttons together to reset system. Set proper program number on apparatus 10 by button P on panel 16 according to microbial tablet label, e.g. 5 as illustrated, incubation time 2:55 minutes.
2. Label test tube 36 (13×100 mm) to identify test samples using marker pen.
3. Draw 0.6 ml supplied distilled water and dispense into test tube.
4. Mix milk test sample vigorously to resuspend fat. Add 0.2 ml milk to each tube, using pipet 40 and a new pipet tip for each sample.
   FIRST TIME USERS: Run a negative control along with samples until familiar with colors. Add negative control tablet to 0.6 ml supplied distilled water. Using pipet and a new pipet tip, add 0.2 ml additional supplied water.
5. Place test tube 36 in holes 26 and 28 of blocks 18 and 20 and press S button to start selected program.
6. When first green light turns on (approx. 6 min., 30 sec. preheat period), tilt apparatus 10 to rest on support 24 and to place block 18 and 20 in contact (see FIGS. 2 and 4) to cool test tube. When second green light turns on (approx. 1 min., 30 sec.), tilt block upright and immediately add one microbial tablet to each test tube by pushing through blister pack into test tube with the blunt end of a pen or pencil. Press I button.
7. When third green light turns on (approx. 1 min, 45 sec.), tilt block down.
8. When fourth green light turns on (approx. 6 min.), tilt block upright and immediately add one medium tablet to each test tube by pushing through blister pack into test tube. Shake test tube from side to side to disperse tablet (5 sec.). Cap test tube and immediately tilt block down.
9. When red light turns on (approx. 2 hrs., 55 min. incubation time), test is complete. (Caution: heating block and test tube may be hot.)
10. Observe color of sample in fluorescent light or daylight and compare to color references to determine positive or negative.

The temperature C.° versus time in minutes graphical profile of the test sample above is illustrated in FIG. 8 (with the additional step of heating the test sample after incubation and observation of the test results to preserve the assay results heat to 90° C. for 2 minutes). FIG. 9 shows the enlarged temperature C.° versus time in minutes graphical profile of a representative test with the time in minutes at each point shown on the graph. This graphical profile is an enlarged portion of the first part of FIG. 8 shown in dotted lines in FIG. 7 for a specific sulfa drug test.

The invention provides a unique sensitive test method for the detection of low concentrations of antimicrobial drugs and other antimicrobial compounds, either manually or by use of the control apparatus illustrated, which test method, test compositions and test kit and control apparatus have many advantages over the present prior art test methods and kits.

What is claimed is:

1. An automatic test apparatus for use in a test method for detection of antimicrobial drugs in a sample, which test apparatus comprises:
   a) a lower metal heating block having a plurality of openings therein for the insertion and holding of one or more test containers to be heated and cooled with a sample therein;
   b) electrical heating means to heat rapidly the heating block, so that one or more of the test containers and samples therein will be heated rapidly to one or more selected temperatures for a defined time period;
   c) an upper metal cooling block to cool rapidly the heated heating block with one or more of the test containers and samples therein to a selected cool temperature, the cooling block having a plurality of openings therethrough which openings are aligned with the plurality of openings of the heating block for the insertion of one or more test containers therethrough and into the openings of the lower heating block, the cooling block being of sufficient mass to cool rapidly the heating block, when the two blocks are placed in a contacting heat exchange relationship;

d) means to move the heating and cooling blocks between a separate, spaced apart, generally horizontal heating position wherein an electrical heating means heats the heating block with one or more test containers therein, to one or more selected heating temperatures, while the heating block is spaced apart from the cooling block, and a contacting, tilted, heat exchange, cooling position wherein the heating block, with one or more test containers therein and extending through the aligned opening in the upper cooling block, is cooled to a selected cool temperature by sliding in the tilted position into direct contact heat exchange with the cooling block, which is at a lower temperature than the heating block; and e) electrical circuitry and programming means to provide for the automatic, timed, sequential heating of the heating block to one or more defined heating temperatures and which includes signal means to signal the timed periods for movement of the heating and cooling blocks by the user between the heating and cooling positions.

2. The test apparatus of claim 1 wherein the heating block and cooling block are composed of aluminum.

3. The test apparatus of claim 1 wherein the heating and cooling blocks contain a plurality of generally uniform, spaced apart, circular openings to receive a plurality of test tubes to be employed as test containers.

4. The test apparatus of claim 1 wherein the means to move the heating and cooling blocks between heating and cooling positions includes:

rod means having one end secured to the cooling block and the other end resting against a surface on which the test apparatus is placed and extending slidably through a hole in the heating block to provide for the heating block to be spaced apart from the cooling block when the test apparatus is in a generally horizontal heating position, and for the heating block and the cooling block to be in direct heat exchange surface contact when the test apparatus is placed in a tilted cooling position with the cooling block sliding into contact with the heating block, so that the cooling block may cool the heated heating block to a lower temperature.

5. The test apparatus of claim 4 wherein the rod means comprises a plurality of rods, secured at each corner of and extending upwardly from the heating block and slidably mounted into aligned holes in the upper cooling block; and a generally centrally positioned, fixed length rod secured to and extending downwardly from the upper cooling block and through an opening in the lower heating block, whereby one lower end of the central rod, when the apparatus is in the generally horizontal position, rests on a support and maintains the lower and upper block in a spaced-apart position, and on tilting of the apparatus to a cooling position the upper cooling block slidably moves on said plurality of rods into a direct heat exchange cooling position.

6. The test apparatus of claim 4 which includes a handle means to move the test apparatus between the generally horizontal heating position and the tilted cooling position.

7. The test apparatus of claim 4 which includes a support leg means to support the apparatus in a tilt position.

8. The test apparatus of claim 1 which includes a housing with a control panel with the heating and cooling blocks on one side of the housing, the lower heating block fixedly secured to the one side of the housing and directly beneath the cooling block and means between the housing and the heating block to insulate the housing from the heating block.

9. The test apparatus of claim 8 wherein the circuitry and programming means includes in the control panel a start (S) means to start a heating time period, a program means (P) to permit the user to select a desired heating time period, and light signal means to indicate to the user the start or termination of a various sequence of timed test steps.

10. The test apparatus of claim 1 which includes a pipet secured by a chain or cable to the test apparatus.

11. The test apparatus of claim 1 which includes comparative standard negative and positive color indicator means, so that the color of the test sample in one or more test containers can be compared with the standard color indicator means to determine test results.

12. The test apparatus of claim 1 wherein the programming means includes means for the user to select and set the proper times of heated incubation and cooling of the test containers.

13. The test apparatus of claim 12 which includes programming means for the user to select and set times for preheating, heating, and cooling steps for the test containers with visual signal means to indicate the start and termination of each step.

* * * * *